(12) United States Patent
York et al.

(10) Patent No.: US 8,509,903 B2
(45) Date of Patent: Aug. 13, 2013

(54) NEUROMODULATION USING ENERGY-EFFICIENT WAVEFORMS

(75) Inventors: Randall York, Cleveland Heights, OH (US); Scott Kokones, Cleveland, OH (US); Keith Carlton, Cleveland, OH (US); Alan Greszler, Bay Village, OH (US)

(73) Assignee: Intelect Medical, Inc., Cleveland, OH (US)

( * ) Notice: Subject to any disclaimer, the term of this patent is extended or adjusted under 35 U.S.C. 154(b) by 173 days.

(21) Appl. No.: 12/479,067

(22) Filed: Jun. 5, 2009

(65) Prior Publication Data

US 2010/0312303 A1 Dec. 9, 2010

(51) Int. Cl.
*A61N 1/36* (2006.01)
*A61N 1/3605* (2006.01)
*A61N 1/36014* (2006.01)
*A61N 1/40* (2006.01)

(52) U.S. Cl.
USPC ............... 607/45; 607/2; 607/68; 607/71

(58) Field of Classification Search
USPC ............................ 607/2, 45, 68, 71
See application file for complete search history.

(56) References Cited

U.S. PATENT DOCUMENTS

| | | | |
|---|---|---|---|
| 6,549,808 B1 | 4/2003 | Gisel et al. | |
| 6,690,974 B2 * | 2/2004 | Archer et al. | 607/45 |
| 6,928,320 B2 | 8/2005 | King | |
| 7,027,852 B2 * | 4/2006 | Helland | 600/375 |
| 7,203,548 B2 | 4/2007 | Whitehurst et al. | |
| 7,333,858 B2 | 2/2008 | Killian et al. | |
| 7,346,382 B2 | 3/2008 | McIntyre et al. | |
| 7,684,866 B2 | 3/2010 | Fowler et al. | |
| 2005/0277998 A1 * | 12/2005 | Tracey et al. | 607/48 |
| 2006/0095088 A1 * | 5/2006 | De Ridder | 607/48 |
| 2006/0122657 A1 | 6/2006 | Deal et al. | |
| 2006/0259098 A1 | 11/2006 | Erickson | |
| 2007/0060974 A1 * | 3/2007 | Lozano | 607/45 |
| 2007/0088393 A1 * | 4/2007 | Ben-Haim et al. | 607/2 |
| 2007/0288064 A1 | 12/2007 | Butson et al. | |
| 2008/0065183 A1 | 3/2008 | Whitehurst et al. | |
| 2008/0215101 A1 | 9/2008 | Rezai et al. | |
| 2009/0069871 A1 | 3/2009 | Mahadevan-Jansen | |
| 2009/0187230 A1 | 7/2009 | Dilorenzo | |

FOREIGN PATENT DOCUMENTS

WO 2009067610 5/2009

OTHER PUBLICATIONS

PCT/US2010/031741 International Search Report and Written Opinion dated Jul. 14, 2010.
PCT/US2010/031744 International Search Report and the Written Opinion of the International Searching Authority dated Jun. 29, 2010.

(Continued)

*Primary Examiner* — Nicole F Lavert
(74) *Attorney, Agent, or Firm* — Kenyon & Kenyon LLP

(57) ABSTRACT

Methods of neuromodulation in a live mammalian subject, such as a human patient. The method comprises applying an electrical signal to a target site in the nervous system, such as the brain, where the electrical signal comprises a series of pulses. The pulses includes a waveform shape that is more energy-efficient as compared to a corresponding rectangular waveform. Non-limiting examples of such energy-efficient waveforms include linear increasing, linear decreasing, exponential increasing, exponential decreasing, and Gaussian waveforms. Also described are apparatuses for neuromodulation and software for operating such apparatuses.

26 Claims, 9 Drawing Sheets

(56) References Cited

OTHER PUBLICATIONS

Baker, et al., "Subthalamic Nucleus Deep Brain Stimulus Evoked Potentials: Physiological and Therapeutic Implications," Movement Disorder, vol. 17, No. 5 (2002), pp. 969-983.

Bhadra, et al., "High-Frequency Electrical Conduction Block of Mammalian Peripheral Motor Nerve," Muscle & Nerve 32: (Dec. 2005), pp. 782-790.

Bhadra, et al., "Simulation of high-frequency sinusoidal electrical block of mammalian myelinated axons," Journal Computer Nueroscience 22: (2007), pp. 313-326.

Butson, et al., "Tissue and Electrode capacitance reduce neural activation vols. during deep brain stimulation," Clinical Neurophysiology 116 (2005), pp. 2490-2500.

Butson et al., "Differences among implanted pulse generator waveforms cause variations in the neural response to deep brain stimulation," Clinical Neurophysiology, vol. 118 (Aug. 2007), pp. 1889-1894.

Fishler, et al., "Theoretical Predictions of the Optimal Monophasic and Biphasic Defibrillation Waveshapes," IEEE Transactions on Biomedical Engineering, vol. 47, No. 1, Jan. 2000, pp. 59-67.

Grill, et al. "Stimulus Waveforms for Selective Neural Stimulation," IEEE Engineering in Medicine and Biology, Jul./Aug. 1995, pp. 375-385.

Jezernik, et al. "Energy-optimal electrical excitation of nerve fibers," IEEE Trans Biomed Eng, 2005, vol. 52, pp. 740-743.

Krasteva, et al., "On the Optimal Defibrillation Waveform—How to Reconcile Theory and Experiment?," IEEE Transactions on Biomedical Engineering, vol. 53, No. 8, Aug. 2006, pp. 1725-1726.

Kuncel, et al., "Selection of stimulus parameters for deep brain stimulation," Clinical Neurophysiology 115 (2004), pp. 2431-2441.

Malkin, et al., "Experimental Verification of Theoretical Predictions Concerning the Optimum Defibrillation Waveform," IEEE Transactions on Biomedical Engineering, vol. 53, No. 8, Aug. 2006, pp. 1492-1498.

Malkin, et al., "Experimental Evidence of Improved Transthoracic Defibrillation With Electroporation-Enhancing Pulses," IEEE Transactions on Biomedical Engineering, vol. 53, No. 10, Oct. 2006, pp. 1901-1910.

McIntyre, et al., "Extracellular Stimulation of Central Neurons: Influence of Stimulus Waveform and Frequency on Neuronal Output," J. Neurophysiol., vol. 88 (2002), pp. 1592-1604.

Sahin, et al., "Non-rectangular waveforms for neural stimulation with practical electrodes," Journal of Neural Engineering 4 (2007), pp. 227-233.

Shepherd, et al., "Electrical stimulation of the auditory nerve: II. Effect of stimulus waveshape on single fibre response properties," Hearing Research 130 (1999), pp. 171-188.

Suárez-Ántola, "Contributions to the study of optimal biphasic pulse shapes for functional electric stimulation: An analytical approach using the excitation functional," Proceedings of the 29th Annual International Conference of the IEEE EMBS CitéInternationale, Lyon, France, Aug. 23-26, 2007, pp. 2440-2443.

Yousif, et al., "The Influence of Reactivity of the Electrode-Brain Interface of the Crossing Electric Current in Therapeutic Deep Brain Stimulation," Neuroscience 156 (2008), pp. 597-606.

\* cited by examiner

NEUROMODULATION USING ENERGY-EFFICIENT WAVEFORMS

TECHNICAL FIELD

The present invention relates to the modulation of neural function using electrical neuromodulation.

BACKGROUND

Electrical neuromodulation has been demonstrated to be useful for a variety of neurologic conditions. As such, attempts have been made to treat brain injury (e.g., due to trauma, hypoxia/anoxia, or stroke) by deep brain electrical stimulation. Commonly, devices for electrical neuromodulation rely on implanted pulse generators which operate on battery power. When the battery becomes depleted, surgical replacement of the battery and/or pulse generator is often necessary. Thus, efforts have been made to extend the battery-operated lifetime of the device, such as improving the battery technology, optimizing electrode materials, and optimizing the circuit configuration. However, there is a need for other ways to prolong battery life in such neuromodulation devices.

SUMMARY

In one aspect, the present invention provides a method for neuromodulation in a live mammalian subject, comprising: applying an electrical signal to a site in the nervous system of the subject, wherein the electrical signal comprises pulses having an energy-efficient waveform. The energy-efficient waveform may be a non-rectangular waveform. The pulses may be current-controlled or voltage-controlled.

In another aspect, the present invention provides a neuromodulation apparatus comprising: an electrode comprising an electrode contact; and an implantable pulse generator coupled to the electrode; wherein the pulse generator is programmed to apply an electrical signal to the electrode contact, the electrical signal comprising pulses having an energy-efficient waveform. The pulse generator may include a battery as a power source. Using the energy-efficient waveforms, the pulse generator may have a battery-operated lifetime of more than 7 years when providing a continuous electrical signal to the electrode contact.

In another aspect, the present invention provides a computer-readable storage medium that stores executable instructions for performing the following: obtaining a set of numeric values that define an energy-efficient waveform; and controlling a pulse generator to apply an electrical signal to an electrode contact, the electrical signal comprising pulses having the energy-efficient waveform.

DETAILED DESCRIPTION

The present invention relates to the modulation of neural function using electrical neuromodulation. In one aspect, the present invention provides a method for neuromodulation in a live mammalian subject, such as a human patient. The modulation of neural function may be useful in treating neurologic conditions, such as, for example, stroke, traumatic brain injury, or Parkinson's disease. The method comprises applying an electrical signal to a target site in the nervous system, such as, for example, the brain, where the electrical signal comprises a series of pulses. The pulses include a waveform shape that is more energy-efficient as compared to a pulse having a rectangular waveform but otherwise being constrained to the same parameter settings as the energy-efficient waveform (i.e., same peak amplitude and same pulse width). As used herein, "rectangular waveform" includes rectangular as well as square waveforms.

The waveform may represent either the current or the voltage of the electrical pulse in the time domain. For current-controlled pulses, if J(t) were to represent the current vs. time function defining the energy-efficient waveform and K(t) were to represent the current vs. time function defining the corresponding rectangular waveform over time t=0 to W (pulse width), then the energy consumed by the pulse waveforms would be proportional to the integral of the square of the current-time functions. This can be expressed with the equations below, where $E_{\mathit{eff}}$ is the proportional energy consumed by the energy-efficient pulse waveform and $E_{\mathit{rect}}$ is the proportional energy consumed by the rectangular pulse waveform having the same pulse width (W) and same peak amplitude, i.e., max(J(t))=max(K(t)) over t=0 to W.

$$E_{\mathit{eff}} \propto \int_0^W J(t)^2 \, dt$$

$$E_{\mathit{rect}} \propto \int_0^W K(t)^2 \, dt$$

For simplicity, the electrode impedance R is omitted from this energy equation since the impedance appears as a scalar for all waveforms (energy being the integral of power, and power being $I^2 R$). For voltage-controlled pulses, the same equations could be used to define the energy consumed except that J(t) would represent the voltage vs. time function for the energy-efficient waveform and K(t) would represent the voltage vs. time function for the rectangular waveform. Again, the electrode impedance R is omitted from the energy equation since the impedance appears as a scalar for all waveforms (energy being the integral of power, and power being $V^2/R$). For both current-controlled and voltage-controlled signals, an energy-efficient waveform will have an $E_{eff}$ that is less than $E_{rect}$.

Figure 1:
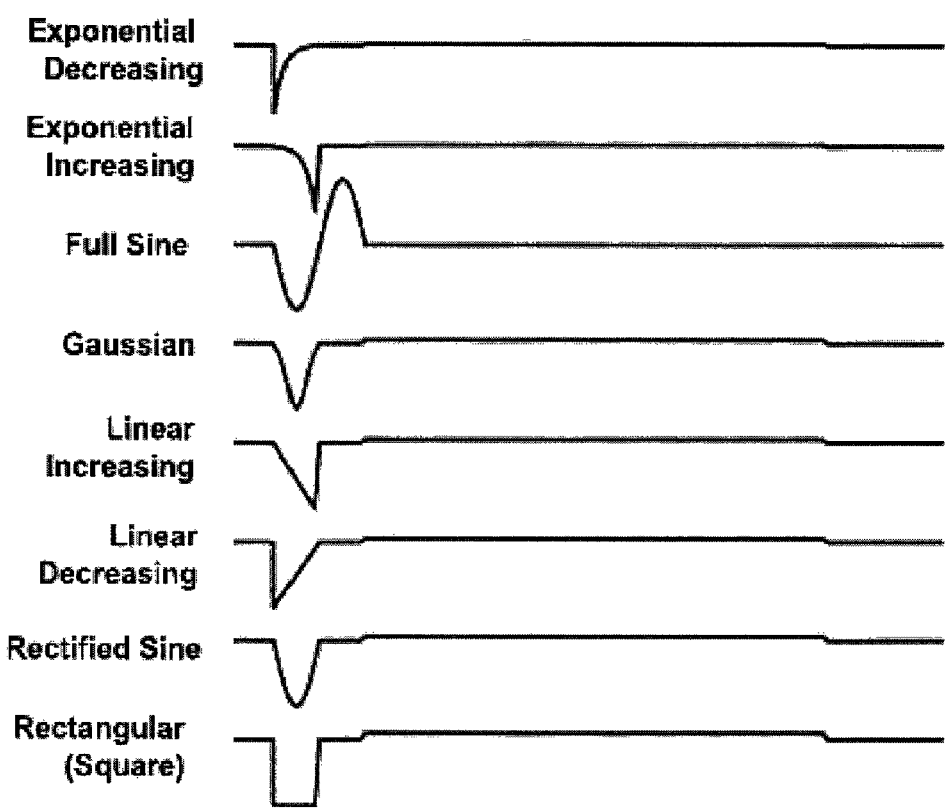
FIG. 1 shows a number of biphasic pulse waveforms, including those that are examples of energy-efficient waveforms of the present invention.

The present invention may employ any of various types of energy-efficient waveforms that are capable of providing effective neuromodulation. In some cases, the energy-efficient waveform is a non-rectangular waveform. FIG. 1 shows a number of biphasic pulse waveforms, including exponential decreasing, exponential increasing, full sine, Gaussian, linear increasing, linear decreasing, and rectified sine as examples of energy-efficient waveforms of the present invention, in comparison to a rectangular waveform shape. For all waveforms shown, except for the full sine waveform, the cathodic pulse is followed by a relatively longer and lower amplitude rectangular-shaped anodic pulse to charge balance the cathodic pulse.

Although the use of energy-efficient waveforms may conserve battery power, prior to the present invention, it was unknown whether such energy-efficient waveforms could provide effective neuromodulation. In fact, according to current understanding of how neuromodulation operates, it would be expected that energy-efficient waveforms would be less effective than conventional rectangular waveforms in activating neural tissue, as explained in the following computational model for predicting volumes of tissue activation. Field-neuron stimulation models for predicting the volume of tissue activation (VTA) by electrical neuromodulation using finite element analysis and neuron computational models have been described in U.S. Pat. No. 7,346,382 (McIntyre et al.) and U.S. Appln. Pub. No. 2007/0288064 (Butson et al.), which are both incorporated by reference herein. For rectangular pulses, this model for predicting VTAs has been validated experimentally through electrophysiologic measurements of neural activity during deep brain stimulation.

This computational model was used to predict the VTA resulting from current-controlled, monopolar stimulation using various pulse waveforms (indicated below) delivered with a Medtronic 3387/3389 deep brain stimulation (DBS) electrode (1.27 mm diameter, 1.5 mm height). The volume of tissue activation was determined in a two-step process. First, the electric field resulting from a chronically implanted DBS electrode was calculated using a finite element model implemented in Comsol 3.2 (Comsol, Burlington, Mass.). Solutions were calculated for 1 mA stimulation in a 1 KΩ impedance tissue volume that incorporated an encapsulation layer around the electrode to represent the chronic foreign body reaction to the implant.

In the second step, the electric field was coupled to a matrix of 5.7 µm diameter myelinated axon models. 119 of the model axons were distributed in a 17×7 matrix oriented perpendicular to the electrode shaft and was used to identify the spatial extent of activation in the vertical and horizontal directions relative to the electrode shaft. The model axons were placed from 1-4 mm lateral to the electrode and from +4 mm above to −4 mm below the center of the electrode contact. Each model axon included 21 nodes of Ranvier with 0.5 mm internodal spacing. The time-dependent stimulation waveform was interpolated onto the length of each cable model, and the time-dependent transmembrane potential variations induced by the stimulation were calculated in NEURON v5.7. Threshold stimulus amplitudes were defined that generated action potentials in a one-to-one ratio with the stimulus frequency. The threshold stimulus values were used to create 2D contours to define the boundary of activation as a function of the stimulus amplitude. These contours were swept around the electrode axis and the theorem of Pappus was used to determine the VTA.

The VTA modeling was performed using various pulse waveforms, including: exponential decreasing, exponential increasing, full sine wave (with the cathodic and anodic phases at a frequency determined from 2× the cathodic phase pulse width), Gaussian, linear increasing, linear decreasing, rectified sine wave (cathodic phase was half of a sinusoid at a frequency of 2× cathodic phase pulse width, and the anodic recharge phase being square), and rectangular. The signal was scaled to a frequency of 100 Hz, cathodic phase pulse width of 100 µs, anodic phase pulse width of 100 µs, interpulse interval of 100 µs, and current in the range of 0-4 mA.

Figure 2:
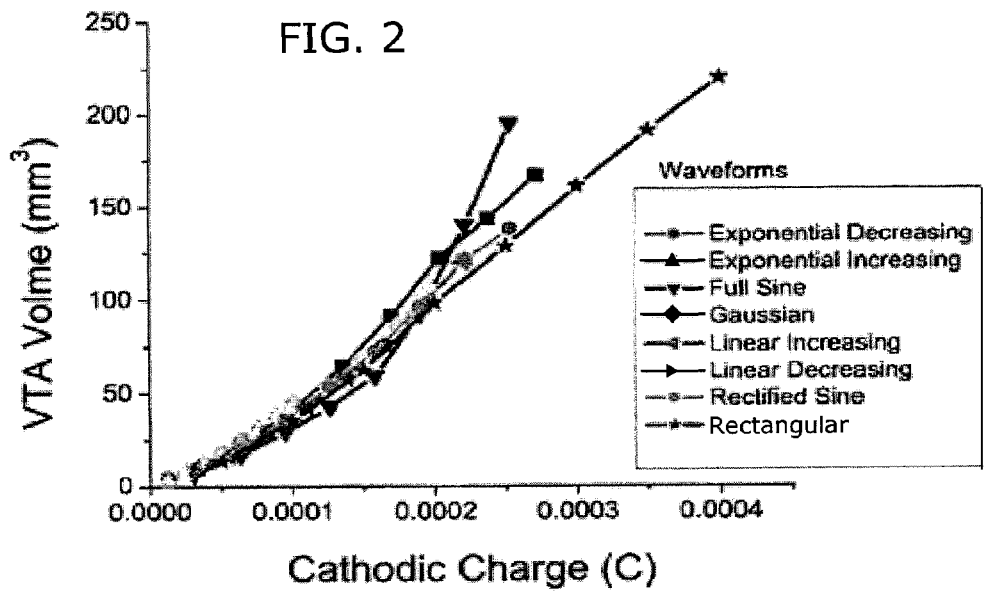
FIG. 2 shows a plot of the calculated volumes of neural tissue activation for various waveforms according to the amount of charge injected.

FIG. 2 shows the calculated VTAs for these waveforms normalized according to the amount of charge injected and the amount of current being varied. These results demonstrate that, at equivalent charge injection levels, the different waveforms do not produce substantially different VTAs. This is expected because it is known that the amount of neural activation is primarily determined by the amount of charge injected, as described in Butson et al., Clinical Neurophysiology 118:1889-1894 (August 2007) and as will be further explained below in the discussion of charge (Q) injected by pulse waveforms.

Figure 3:
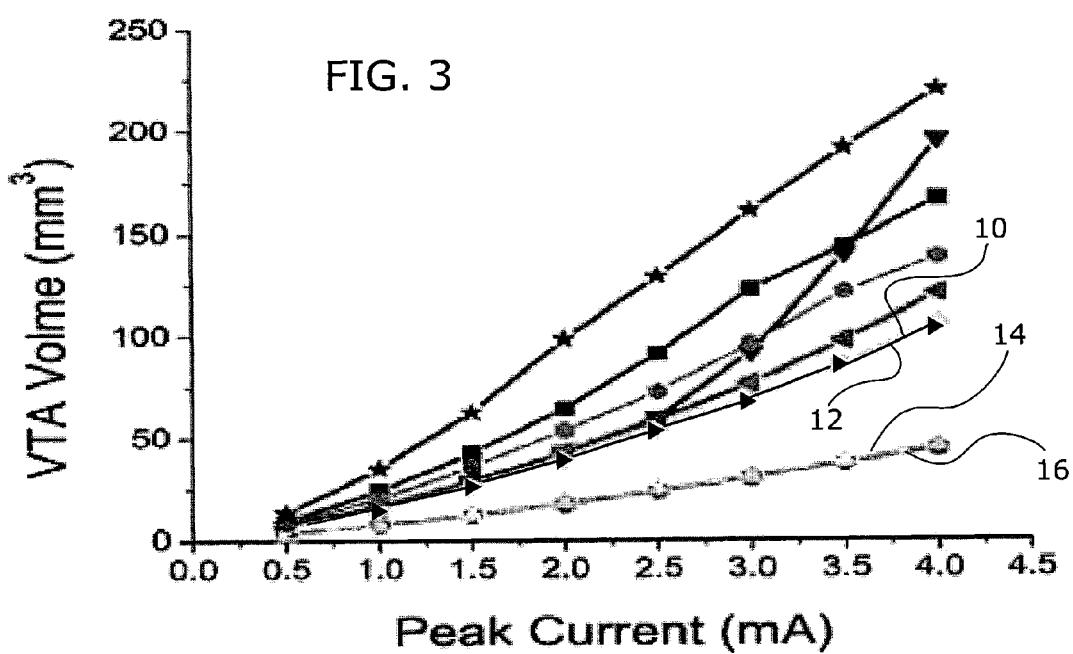
FIG. 3 shows a plot of the calculated volumes of neural tissue activation for various waveforms according to the amount of current.

FIG. 3 shows the calculated VTAs for the above waveforms normalized according to the peak current and the amount of charge injection being varied. For enhanced clarity, reference numbers are added to indicate the plots for linear decreasing 10, Gaussian 12, exponential increasing 14, and exponential decreasing 16. At equivalent peak amplitudes, energy-efficient waveforms will provide less charge injection than rectangular waveforms. Given that neural activation is predicted to correlate with the amount of charge injection, FIG. 3 indicates that all the energy-efficient waveforms would have lower VTAs as compared to the rectangular waveform. The exponential decreasing and exponential increasing waveforms have the lowest predicted VTAs.

Based on these computational modeling results, energy-efficient waveforms would be expected to provide less effective neuromodulation than the rectangular waveform. However, as will be demonstrated below, this is not the case. Energy-efficient waveforms provide neuromodulation that is at least as effective as neuromodulation using rectangular waveforms. Furthermore, although the computational models predict the amount of axonal activation by the energy-efficient waveforms, prior to the present invention, it was unknown whether axonal activation would translate to trans-synaptic neuronal activation in vivo in a sustained and functional manner.

By conserving battery power, devices of the present invention may provide continuous, long-term neuromodulation of more than 7 years (in some cases, up to 10 or 15 years) before the battery needs to be replaced. However, other operating lifetimes are also possible. In addition to energy conservation, there may also be other benefits to using energy-efficient waveforms for neuromodulation. For example, the energy-efficient waveforms can provide increased discriminability in neural activation (more precise neural activation per unit current or voltage of the waveform) as compared to rectangular waveforms. Referring back to FIG. 3, the slope of the plot for the energy-efficient waveforms are shallower than the slope of the plot for the rectangular waveform. With a relatively steep slope of 60.8, the rectangular waveform had the least discriminability. With a relatively shallow slope of 11.8, the exponential increasing and exponential decreasing waveforms had the highest discriminability.

Having higher discriminability may be useful in obtaining finer control of the VTA. Precise control of VTA may be desirable to avoid stimulation of areas that could cause negative side effects.

As explained above, energy-efficient waveforms may provide effective electrical neuromodulation with reduced charge injection as compared to neuromodulation using the corresponding rectangular waveform. For current-controlled pulses, the amount of charge (Q) delivered by the pulse waveform can be expressed with the equations below, where J(t) is the current vs. time function defining the energy-efficient waveform and K(t) is the current vs. time function defining the corresponding rectangular waveform over time t=0 to W (pulse width). $Q_{eff}$ is the charge delivered by the energy-efficient pulse waveform and $Q_{rect}$ is the charged delivered by the rectangular pulse waveform having the same pulse width (W) and the same peak amplitude, i.e., max(J(t))=max(K(t)) over t=0 to W.

$$Q_{eff} = \int_0^W |J(t)| dt$$

$$Q_{rect} = \int_0^W |K(t)| dt$$

An energy-efficient waveform can provide reduced charge injection such that $Q_{eff}$ is less than $Q_{rect}$. In some case, the charge injection is reduced such that $Q_{eff}$ is one-half or less of $Q_{rect}$, and in some cases, one-third or less of $Q_{rect}$.

Reduced charge injection can be advantageous in several ways. One potential advantage is that higher peak currents at higher charge densities can be used to enhance neural activation, but with less concern over neural damage since the overall amount of charge injected is reduced.

The energy-efficient waveforms can also allow for more neural activation per unit electrode surface area. This can allow for smaller electrode designs for the same neuromodulation effect in tissue (i.e., a more effective use of electrode area). As such, electrodes used in the present invention may be designed to have a surface area of 5 mm$^2$ or less, and in some cases, 1.25 mm$^2$ or less. But other electrode surface areas are also possible.

The energy-efficient waveforms may also be relatively less affected by the reactance at the electrode-brain interface (EBI). The results of computational modeling studies have indicated that the waveforms applied by an electrode implanted in the brain becomes attenuated due to reactance at the EBI, and this attenuation varies over time due to changes in the EBI. But Yousif et al. also report that linear decreasing, exponential decreasing, and Gaussian waveforms are less attenuated by the EBI than are square waveforms. With reduced EBI attenuation, the idealized waveform as determined by the waveform parameters will more closely represent the waveform that is actually induced in the neural tissue. This can improve the ability to make correlations and interpretations of behavioral and physiological data during and after electrode implantation for the optimization of parameter settings.

The electrical signal or pulse waveform may be characterized according to various parameters, including voltage, current amplitude, pulse width, average pulse frequency, or train length. Such parameters will vary depending upon the particular application. For example, the voltage may be selected from a range of ±0.1 to 10V, pulse width may be selected from a range of 10-1000 µs per phase, average pulse frequency may be selected from a range of 20 to 2000 Hz, and current may be selected from a range of ±0.1 µA to 5 mA.

The pulse may be monophasic, biphasic, multiphasic, etc. The pulse may be symmetric or asymmetric. For example, in the case of a biphasic pulse, the negative phase and the positive phase may have identical shapes but of opposite polarity for charge balancing. However, it is also possible for the biphasic pulse to be asymmetric and still be charged balanced. For example, the positive phase may have a longer duration but smaller amplitude than the negative phase such that the injected charge is balanced. Where a pulse is biphasic or multiphasic, one or more of the phases can have an energy-efficient waveform. For example, in the case of a biphasic pulse, either the cathode pulse, or the anodic pulse, or both may have an energy-efficient waveform. The pulse may be current-controlled, voltage-controlled, or a combination of both. The pulse may be analog or digitally generated.

Figures 4A, 4B:
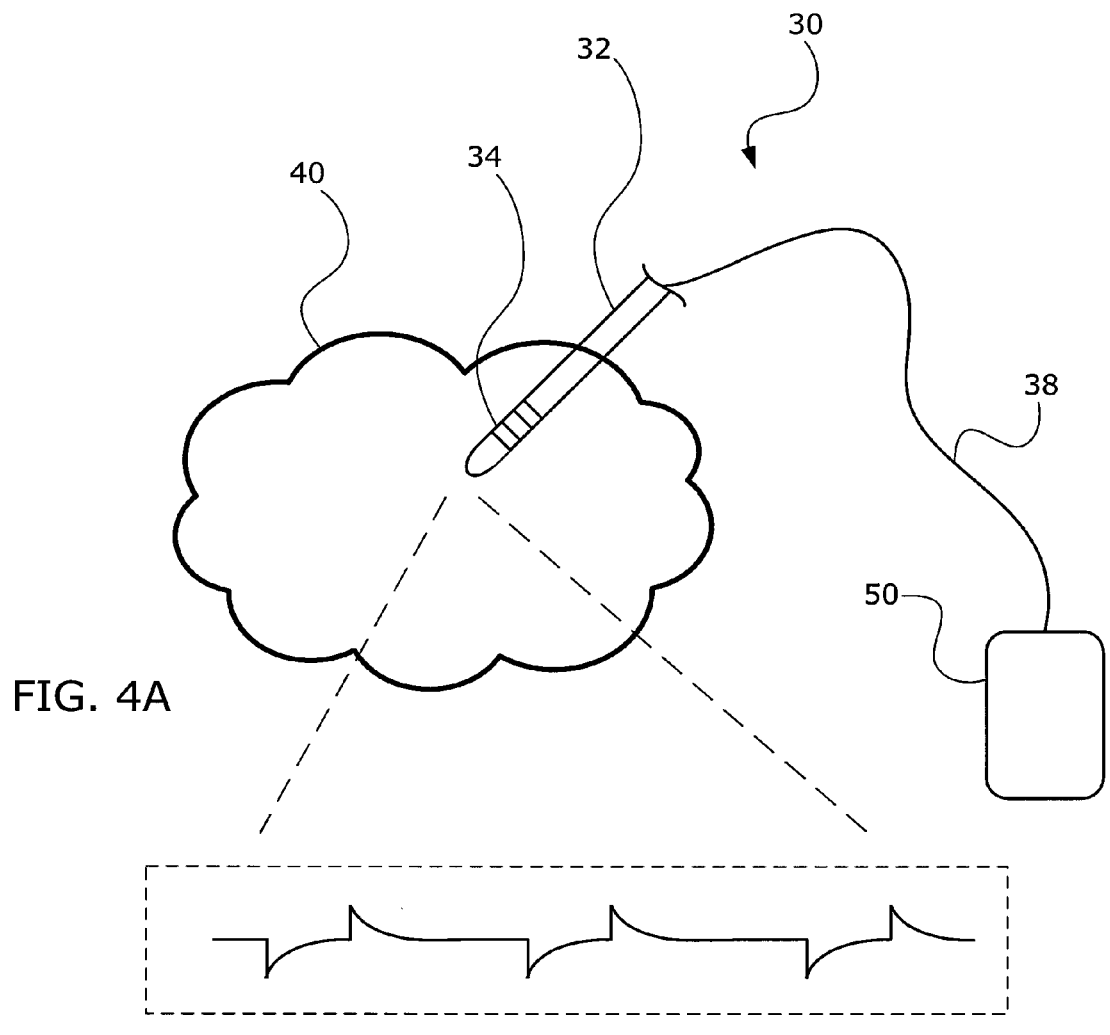
FIG. 4A shows a neuromodulation apparatus according to an embodiment of the present invention.
FIG. 4B shows a portion of the signal being applied by the neuromodulation apparatus.

Referring to the example embodiment shown in FIGS. 4A and 4B, a neuromodulation apparatus 30 includes an electrode 32 having electrode contacts 34, which is implanted in a brain site 40. A lead extension 38, which travels in a subcutaneous tunnel created by blunt dissection, connects electrode contacts 34 to a pulse generator 50 implanted, for example, in a subcutaneous pocket in the patient's chest area. As such, electrode contacts 34 are coupled to pulse generator 50. As used herein, the term "coupled" refers to a signaling relationship between the components in question, including direct connection or contact (e.g., via an electrically or optically conductive path), radio frequency (RF), infrared (IR), capacitive coupling, and inductive coupling to name a few. Pulse generator 50 is programmed to generate an electrical signal having, for example, the exponential decreasing waveform shown in FIG. 4B. This signal is transmitted via lead extension 38 to electrode contacts 34 on electrode 32. Pulse generator 50 also includes a battery (not shown) serving as a power source.

The electrode used for delivering the electrical signal may be any of those known in the art that are suitable for use in electrical neuromodulation. The design characteristics of the electrode will vary depending upon the needs of the particular application, including such features as the number, direction, position, and/or arrangement of electrode contacts on the electrode; number of independent channels; and geometry and/or configuration of the electrode. Also, as mentioned above, use of energy-efficient waveforms can allow for smaller electrode designs for the same neuromodulation effect as compared to rectangular waveforms.

Figure 5:
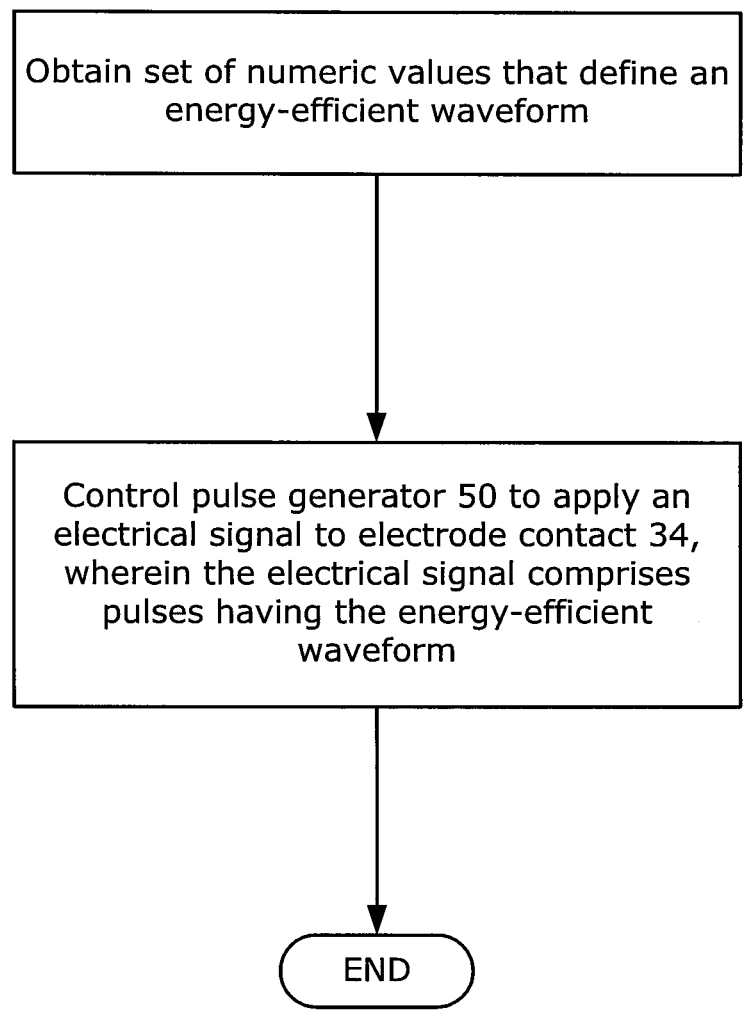
FIG. 5 shows a flowchart of the operation of the neuromodulation apparatus shown in FIG. 4.

The various functions and capabilities of neuromodulation apparatus 30 may be performed by electronic hardware, computer software (or firmware), or a combination of both. As such, neuromodulation apparatus 30 may include a computer-readable storage medium having executable instructions for performing the various processes as described and illustrated herein. The storage medium may be any type of computer-readable medium (i.e., one capable of being read by a computer), such as hard drive memory, flash memory, floppy disk memory, or optically-encoded memory (e.g., a compact disk, DVD-ROM, DVD±R, CD-ROM, CD±R). The systems disclosed herein may also include addressable memory (e.g., random access memory or cache memory) to store data and/or sets of instructions that may be included within, or be generated by, the executable instructions when they are executed by a processor on the respective platform. For example, pulse generator 50 may have executable instructions for performing the calculations needed to produce the desired neuromodulation signal. FIG. 5 shows a flowchart of how a neuromodulation apparatus may be operated according to an embodiment of the present invention.

In certain embodiments, the pulse generator is pre-programmed to deliver an electrical signal of a predetermined pattern to modulate neural function as described below or to treat neural conditions or disorders as described below. In a preferred embodiment, the pulse generator is pre-programmed to deliver an electrical signal of a predetermined pattern to improve the function(s) (cognitive, motor, psychiatric, or other deficient functions) of a patient suffering from stroke, traumatic brain injury, or a neurodegenerative disease such as Parkinson's disease or Alzheimer's disease.

The present invention can be used for neuromodulating a site in the nervous system of a live mammalian subject. Such neuromodulation includes activating neural tissue (which can be stimulatory or inhibitory) and includes modulating neural functions such as stimulating, depressing, or enhancing neural function (abnormal or normal) or treating neural conditions and disorders.

The electrical neuromodulation can be applied to the peripheral nervous system or the central nervous system, such as the brain or spinal cord. The electrical neuromodulation can be applied to various sites in the brain, depending upon the particular application. In some cases, the electrical neuromodulation is applied to a site in the brain that is involved in motor function, to treat, for example, motor disorders such as Parkinson's disease, tardive dyskinesia, spasticity, bradykinesia, essential tremor, stroke, Tourette's syndrome and other motor function disorders. Such sites in the brain that are involved in motor function include, for example, the basal ganglia (e.g., subthalamic nuclei or globus pallidus, such as the internal globus pallidus or the external globus pallidus), the thalamus (e.g., ventral anterior nuclei, ventral lateral nuclei, ventral posteriolateral nuclei, ventral intermediate nuclei, intralaminar nuclei, or medial dorsal nuclei), the cerebellum (to treat stroke, for example), dentatothalamocortical pathway (DTC) (e.g., dentate nuclei or superior cerebellar peduncle), corpus callosum (to treat stroke, for example). In some cases, the electrical neuromodulation is applied to a site in the brain that is involved in arousal or cognitive function (e.g., central thalamus, intralaminar nuclei, or subthalamic nuclei) to treat, for example, cognitive dysfunction resulting from traumatic brain injury.

In preferred embodiments, the neurologic disorders are stroke, traumatic brain injury, neurodegenerative disease (e.g., Alzheimer's disease and Parkinson's disease), movement disorder (e.g., Parkinson's disease, essential tremor, tardive dyskinesia, and Tourette's syndrome), or psychiatric disorders (e.g., depression, obsessive compulsive disorder, addictions). In certain preferred embodiments, the methods of the present invention are used to improve cognitive, psychiatric, motor, and/or other functions in patients suffering from stroke and/or traumatic brain injury. In some embodiments, the neurologic disorders or conditions treated by the present invention are characterized by motor dysfunction. Such neurologic disorders or conditions that can involve motor dysfunction include, for example, Parkinson's disease, stroke, or traumatic brain injury.

Further examples of neurologic conditions and target sites that can be treated by the present invention are provided in Table 1 below.

TABLE 1

| Neurologic Condition | Specific Examples of Neurologic Conditions | Target Sites in the Brain for Treating the Conditions Identified in the Columns on the Left Side |
|---|---|---|
| Motor disorders | Parkinson's disease, tardive dyskinesia, spasticity, bradykinesia, essential tremor, stroke, Tourette's syndrome, ataxia, akinesia, athetosis, ballismus, hemiballismus, bradykinesia, dystonia, chorea including Huntington's disease, multiple system atrophies (e.g., Shy-Drager syndrome), myoclonus, progressive supranuclear palsy, restless leg syndrome and periodic limb movement disorder, tics, tremor (e.g., essential tremor, resting tremor), Wilson disease, tardive dyskinesia, and paralysis or weakness due to stroke or other cortical injury | basal ganglia (e.g., subthalamic nuclei or globus pallidus, such as the internal globus pallidus or the external globus pallidus), the thalamus (e.g., ventral anterior nuclei, ventral lateral nuclei, ventral posteriolateral nuclei, ventral intermediate nuclei, intralaminar nuclei, or medial dorsal nuclei), the cerebellum, dentatothalamocortical pathway (e.g., dentate nuclei or superior cerebellar peduncle), corpus callosum. |
| Arousal, psychiatric, or cognitive dysfunctions | traumatic brain injury, obsessive compulsive disorder, addictions, depression, anxiety disorder, autism, dyslexia, generalized anxiety disorder, post traumatic stress disorder, panic attack, social phobia, major depression, bipolar disorder, schizophrenia, attention deficit disorder, substance abuse disorder, substance abuse addiction | central thalamus, intralaminar nuclei, subthalamic nuclei, pre-frontal cortex, orbitofrontal cortex, anterior limb of the internal capsule, nucleus accumbens, ventral striatum, ventral pallidum, anterior nucleus of the thalamus, dorsomedial nucleus of the thalamus, intralaminar thalamic nuclei, cingulate cortex, amygdala, hippocampus, mammillary bodies, lateral hypothalamus, locus coeruleus, dorsal raphe nucleus, ventral tegmentum, substantia nigra pars compacta, substantia nigra pars reticulata. |

TABLE 1-continued

| Neurologic Condition | Specific Examples of Neurologic Conditions | Target Sites in the Brain for Treating the Conditions Identified in the Columns on the Left Side |
|---|---|---|
| Neurodegenerative diseases | Parkinson's disease, amyotrophic lateral sclerosis (ALS), Guillan Barre, Huntington's disease, multiple system atrophies (e.g., Shy-Drager syndrome), progressive supranuclear palsy | basal ganglia (e.g., subthalamic nuclei or globus pallidus, such as the internal globus pallidus or the external globus pallidus), the thalamus (e.g., ventral anterior nuclei, ventral lateral nuclei, ventral posteriolateral nuclei, ventral intermediate nuclei, intralaminar nuclei, or medial dorsal nuclei), the cerebellum, dentatothalamocortical pathway (e.g., dentate nuclei or superior cerebellar peduncle), corpus callosum. |

EXAMPLES

Experimental trials were conducted in which rats were subjected to electrical neuromodulation using energy-efficient waveforms. The energy-efficient waveforms selected for use in the trials were the following: linear decreasing, exponential decreasing, and Gaussian. The exponentially decreasing and Gaussian waveforms were defined as current amplitude (y) versus time functions as follows:

The exponential decreasing waveform was defined by the following equation:

$$y = Ae^{-\frac{5t}{W}},$$

where y is the current amplitude, A is the desired peak amplitude, W is the desired pulse width, and t is time from 0 to W.

The Gaussian waveform was defined by the following equation:

$$y = Ae^{-\sigma\left(t-\frac{W}{2}\right)^2},$$

where y is the current amplitude, A is the desired peak amplitude, W is the desired pulse width, σ is set to 0.05/W, and t is time from 0 to W. The charge injected by this Gaussian waveform is about 75% of that of the corresponding rectangular waveform.

Figure 6A:
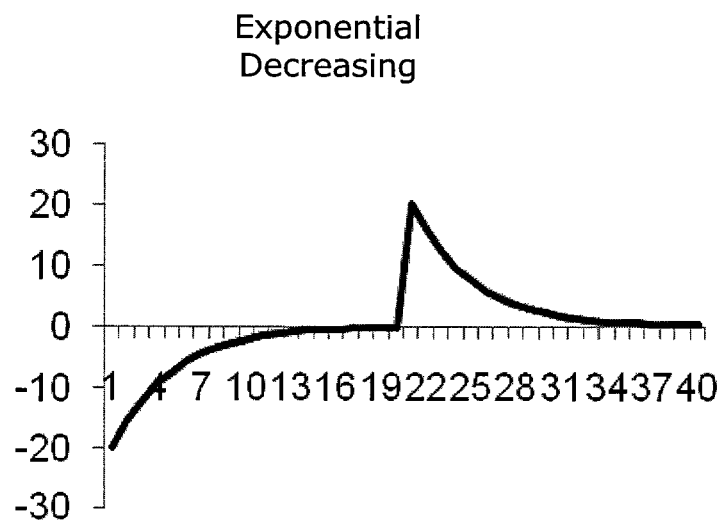
FIG. 6A shows the shape of an exponential decreasing waveform according to an embodiment of the present invention.
Figure 6B:
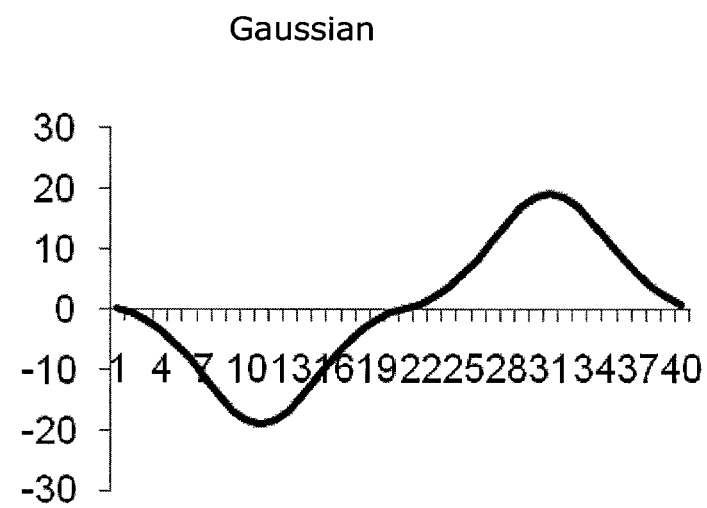
FIG. 6B shows the shape of a Gaussian waveform according to an embodiment of the present invention.

These equations were entered into MATLAB® (MathWorks, Natick, Mass.) to calculate the desired waveform shape as a series of 20 discrete step-values of current at 20 discrete time points for each phase using a peak amplitude of 20 mA. FIGS. 6A and 6B show a plot of the waveforms. FIG. 6A shows the plot of the exponential decreasing waveform, and FIG. 6B shows the plot of the Gaussian waveform. The rectangular and linear decreasing waveforms were not pre-calculated because they are pre-programmed in the neurostimulation system that was used, as explained below.

The set of calculated current step-values for the exponential decreasing and Gaussian waveforms was then imported into the programming software for the neurostimulation system. Once the waveforms are stored in the system, the system allows for waveforms to be further scaled to the desired peak amplitude and pulse width. Since the linear and rectangular waveforms were pre-programmed, there was no need to import those waveforms into the system.

Electrodes were surgically implanted into the brains of 20 rats for deep brain stimulation. The site of electrode implantation was the central lateral (CL) nucleus of the thalamus (AP: −2.8 mm/L:±1.25 mm/V:−5.5 mm). One week after electrode implantation, the rats were assigned to one of 5 different groups (4 rats per group) defined by the stimulation parameters to be delivered: unstimulated (control), stimulation with biphasic rectangular wave (control group), stimulation with biphasic linear decreasing, stimulation with biphasic exponential decreasing, and stimulation with biphasic Gaussian waveforms.

The rats were stimulated using an Intelect Variable Waveform Generator, which was programmed to provide current-controlled pulses using the defined waveforms scaled to 500 μA peak current, 60 μs per phase pulse duration, and 175 Hz frequency. The rats were stimulated for 30 minutes using the selected waveform. Two hours after the initiation of stimulation, the rats were sacrificed, their brains harvested, and processed for histological analysis. Nissl staining (Cresyl violet) confirmed electrode placement. Brain slices at the anterior cingulate cortex were then immunostained for expression levels of c-fos, which is a marker of neural activation.

Figure 7:
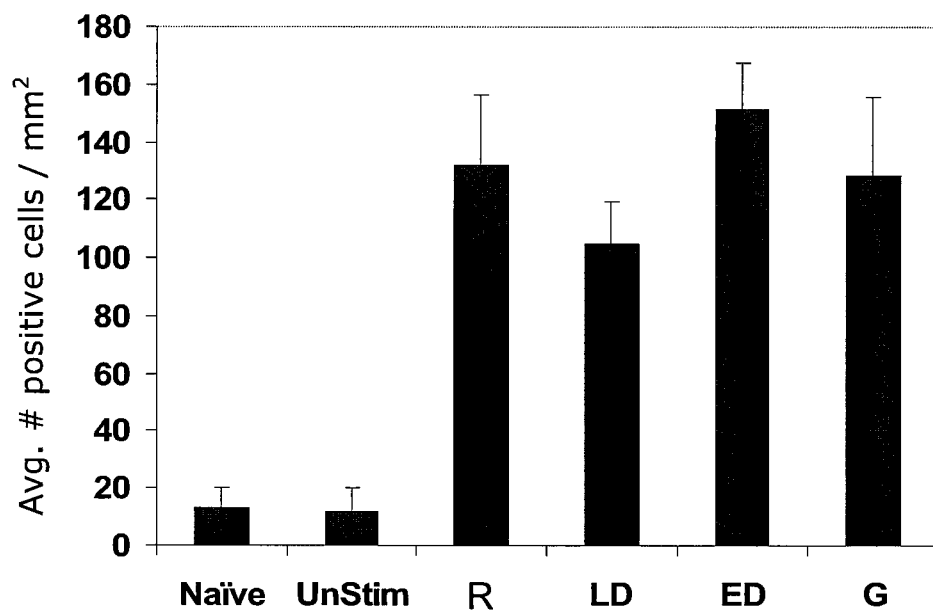
FIG. 7 shows a bar graph of the number of c-fos positive cells detected per square milliliter in the anterior cingulate cortex of rats that underwent neuromodulation trials, as described in more detail herein.

FIG. 7 shows a bar graph of the number of c-fos positive cells detected per square millimeter. "Naïve" refers to rats without electrode implants; "Unstim" refers to rats that had electrode implants, but without electrode stimulation (sham procedure); "R" refers to biphasic square stimulation; "LD" refers to linear decreasing stimulation; "ED" refers to exponential decreasing stimulation; and "G" refers to Gaussian stimulation. These results demonstrate that the efficacy of neuromodulation using energy-efficient waveforms is comparable to that of conventional square waveform pulses.

Further experiments were conducted on rat models of Parkinson's disease. The rats were injected with 6-hydroxydopamine (6-OHDA) into the left medial forebrain bundle. After 4 weeks, the rats were confirmed to exhibit hemi-parkinsonian symptoms by behavioral and motor function testing. The unilateral lesioning was also later confirmed by immunohistochemical analysis of the substantia nigra at the end of the trial.

Electrodes were then surgically implanted into the subthalamic nucleus (STN) on the left side (i.e., ipsilateral to the 6-OHDA lesion). One week after implantation, the rats were subjected to electrical stimulation using one of the four different waveforms mentioned above scaled to deliver 150 µA peak amplitude with a pulse width of 80 µs for each phase at 130 Hz frequency.

The stimulation and behavioral testing protocol was as follows: Each rat was subjected to stimulation using each one of the stimulation waveforms in a randomly-ordered sequence. During stimulation, the rats were tested for forelimb use as further described below. After 2 hours of rest, the rat was again stimulated with the same waveform and tested for vibrissae-induced forepaw placement as further described below. After 2 hours of rest, the rat was again stimulated with the same waveform during testing for apomorphine-induced rotational responses. After this series of stimulation and testing, the rat was then returned to its home cage. After 48-72 hours of rest, the rat was stimulated with the next waveform in the randomly-ordered sequence with this same protocol. This continued until all the rats were tested for each waveform. Table 1 below summarizes the stimulation protocol that was used (ED=exponential decreasing, G=Gaussian, LD=linear decreasing, R=rectangular).

TABLE 1

Stimulation order.

| Animal ID | Baseline | StimA | StimB | StimC | StimD |
|---|---|---|---|---|---|
| 6-OHDA #1 | No Stim | ED | G | R | LD |
| 6-OHDA #2 | No Stim | ED | G | R | LD |
| 6-OHDA #3 | No Stim | R | ED | LD | G |
| 6-OHDA #4 | No Stim | G | R | ED | LD |
| 6-OHDA #5 | No Stim | ED | G | LD | R |
| 6-OHDA #6 | No Stim | R | LD | ED | G |
| 6-OHDA #7 | No Stim | R | G | ED | LD |
| 6-OHDA #8 | No Stim | G | R | LD | ED |
| 6-OHDA #9 | No Stim | G | R | ED | LD |
| 6-OHDA #10 | No Stim | R | ED | G | LD |
| 6-OHDA #11 | No Stim | G | R | LD | ED |
| 6-OHDA #12 | No Stim | G | LD | R | ED |
| 6-OHDA #13 | No Stim | G | LD | R | ED |
| 6-OHDA #14 | No Stim | ED | LD | G | R |
| 6-OHDA #15 | No Stim | ED | R | LD | G |
| 6-OHDA #16 | No Stim | G | LD | R | ED |
| Control-SD #1 | No Stim | ED | G | R | LD |
| Control-SD #2 | No Stim | ED | G | R | LD |
| Control-SD #3 | No Stim | G | LD | ED | R |

Figure 8:
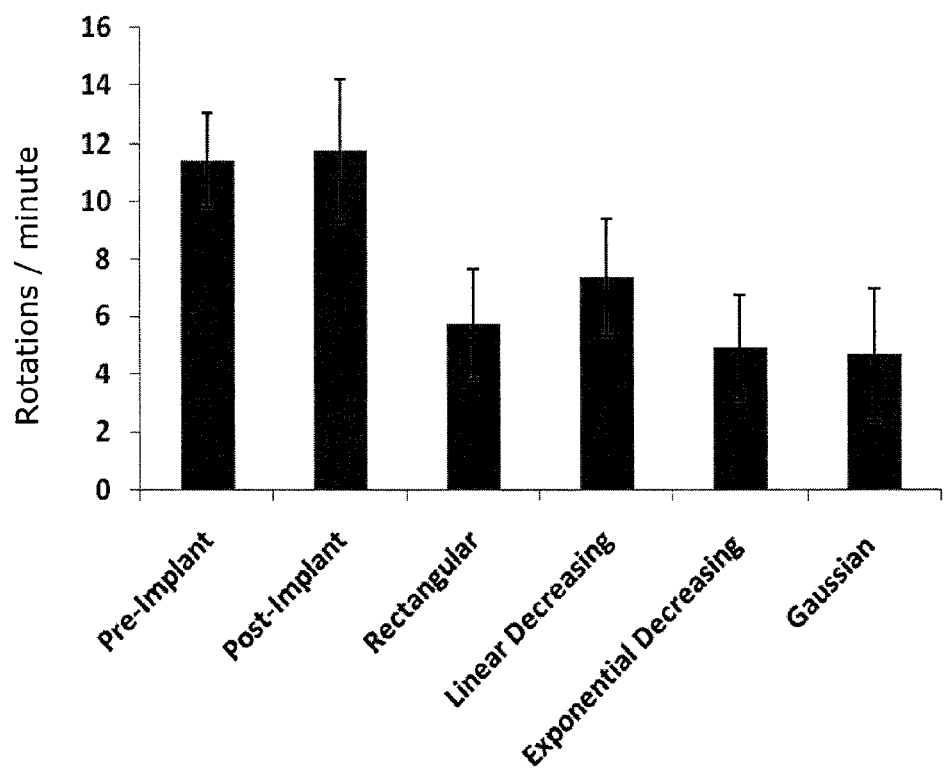
FIG. 8 shows the results from apomorphine-induced rotational response testing, as described in more detail herein.
Figure 9:
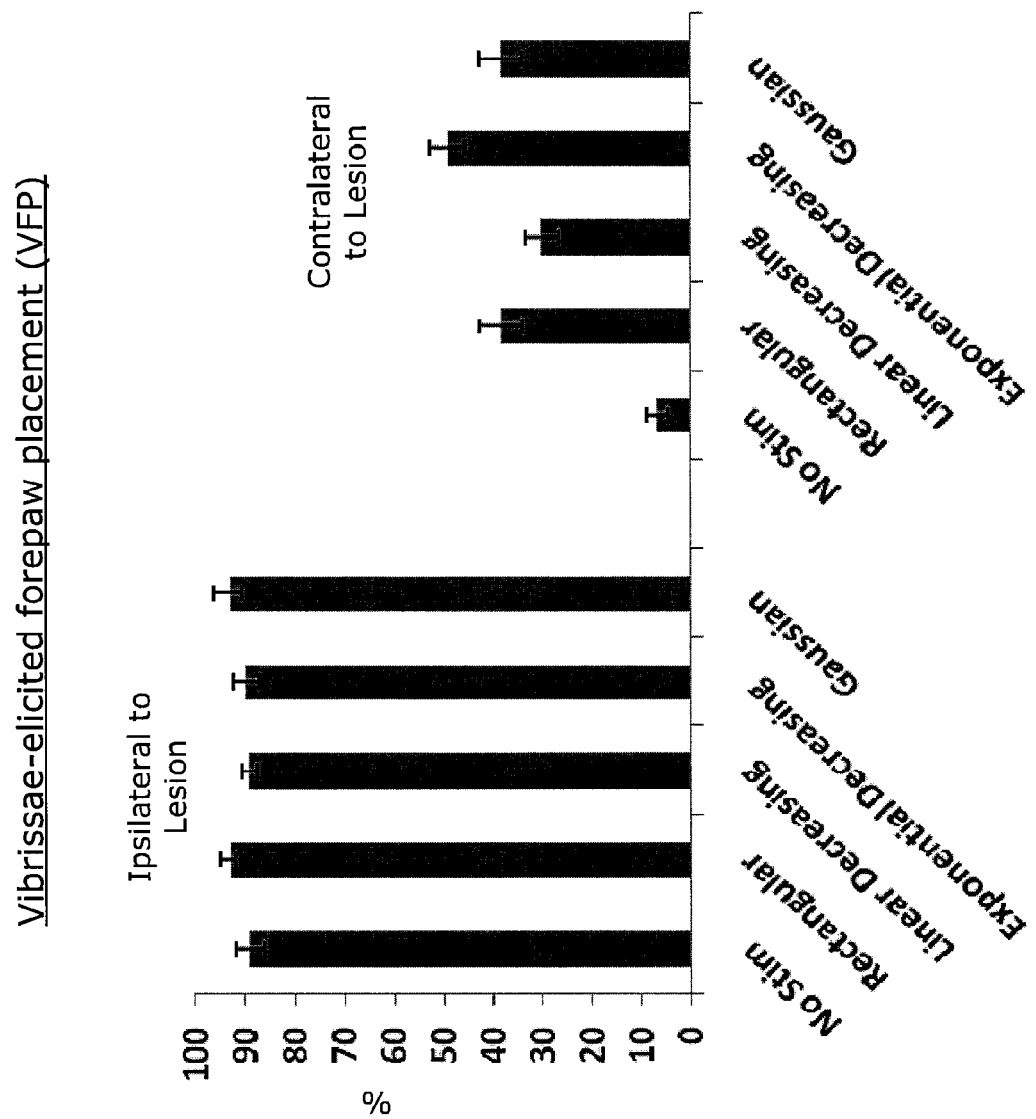
FIG. 9 shows the results of vibrissae-induced forepaw placement testing, as described in more detail herein.
Figure 10:
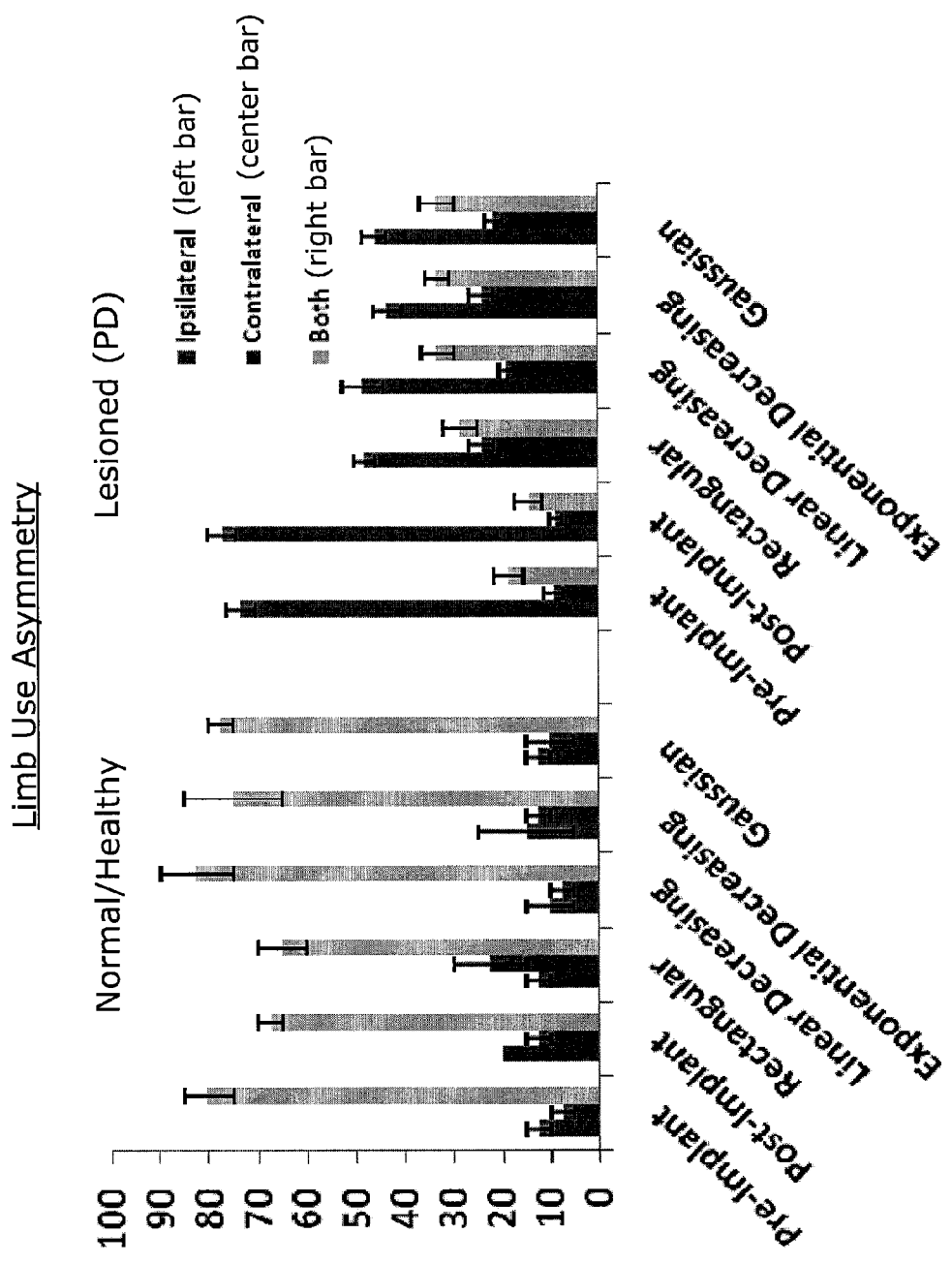
FIG. 10 shows the results from forelimb use testing, as described in more detail herein.

FIGS. 8-10 show the results of these experiments. FIG. 8 shows the results from the apomorphine-induced rotational response (APIR) testing. The bar graph shows the number of net contraversive rotations per minute determined from 10 minute trials periods. Where lesioned appropriately, rats will display about 10 net contraversive rotations per minute, and rats displaying more than 15 net contraversive rotations per minute suggests the possibility of non-specific lesioning and were thus excluded. The results of the pre-implant and post-implant period (without stimulation) confirmed that the rats has parkinsonian deficits. These results also demonstrate that all four waveforms attenuated the rotational response to apomorphine. Notably, the three energy-efficient waveforms (linear decreasing, exponential decreasing, and Gaussian) had substantially the same efficacy as the conventional rectangular waveform stimulation (p>0.05).

FIG. 9 shows the results of vibrissae-elicited forepaw placement (VFP) testing, which is based on the impaired orientation of hemi-parkinsonian rats to contralateral vibrissae stimulation. As seen in the left panel of FIG. 9, vibrissae-stimulation on the side ipsilateral to the 6-OHDA lesion elicited normal or near normal forepaw responses. As seen in the right panel, contralateral forepaw placement was impaired due to the 6-OHDA lesioning. However, this forepaw placement impairment was partially restored following electrical stimulation in the STN (compare with unstimulated rats). Notably, the exponential decreasing waveform was substantially more effective at restoring vibrissae-induced forepaw placement than the linear decreasing waveform (p<0.01). There was no significant difference in efficacy between the rectangular, exponential decreasing, and Gaussian waveforms (p>0.5).

FIG. 10 show the results from the forelimb use testing. The rats were placed inside a cylinder and evaluated for forelimb use during exploratory activity inside the cylinder as determined by the number of independent weight bearing wall contacts for each forelimb. The rats were observed for 3-15 minutes until a total of 20 contacts were made (one rat was excluded for lack of sufficient activity). These 20 forelimb contacts were categorized as either ipsilateral to the lesion site (I), contralateral to the lesion site (C), or near simultaneous use of both (B) forelimbs. Normal/healthy rats predominantly used both forelimbs simultaneously for wall contact, whereas the lesioned rats predominantly used the ipsilateral limb. As seen in the right panel of FIG. 10, electrical stimulation in the STN increased independent use of the impaired contralateral limb (p<0.001 for rectangular and exponential decreasing waveforms; p<0.01 for Gaussian; p<0.05 for linear decreasing) and simultaneous use of both limbs (p<0.001 for exponential decreasing, linear decreasing, and Gaussian; p<0.005 for rectangular), while decreasing use of the ipsilateral alone (p<0.001 for all waveshapes).

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method for neuromodulation in a live mammalian subject, comprising:
    applying an electrical signal to a site in a nervous system of the subject, wherein the electrical signal comprises pulses consisting of an energy-efficient waveform selected from the group consisting of exponential increasing, exponential decreasing, and Gaussian.

2. The method of claim 1, wherein the energy-efficient waveform is exponential decreasing or Gaussian.

3. The method of claim 1, wherein the energy-efficient waveform is exponential decreasing or exponential increasing.

4. The method of claim 1, wherein the pulses are current-controlled pulses.

5. The method of claim 1, wherein the pulses are voltage-controlled pulses.

6. The method of claim 1, wherein the pulses are both current-controlled and voltage-controlled.

7. The method of claim 1, wherein the amount of charge injected by the energy-efficient waveform is one-half or less of the amount of charge injected by a corresponding rectangular waveform having the same peak amplitude and same pulse width.

8. The method of claim 1, wherein the nervous system site is a site in the brain involved in motor function.

9. The method of claim 8, wherein the brain site is the thalamus or subthalamic nucleus.

10. The method of claim 1, wherein the energy-efficient waveform is analog or digitally generated.

11. A method of treating a neurologic condition in a live mammalian subject, comprising the method of claim 1.

12. The method of claim 11, wherein the neurologic condition is traumatic brain injury, stroke, a neurodegenerative disease, a movement disorder, or a psychiatric disorder.

13. The method of claim 11, wherein the neurologic condition involves an impairment of motor function.

14. The method of claim 11, wherein the neurologic condition is Parkinson's disease, the site in the nervous system is the subthalamic nucleus, and the energy-efficient waveform is exponential decreasing.

15. The method of claim 11, wherein the neurologic condition involves a motor dysfunction.

16. The method of claim 1, wherein the nervous system site is a site in the brain involved in arousal or cognitive function.

17. The method of claim 16, wherein the brain site is the central thalamus, intralaminar nuclei, or subthalamic nuclei.

18. The method of claim 11, wherein the nervous system site is selected from the group consisting of: basal ganglia, subthalamic nuclei, globus pallidus, internal globus pallidus, external globus pallidus, thalamus, central thalamus, intralaminar nuclei, ventral anterior nuclei, ventral lateral nuclei, ventral posteriolateral nuclei, ventral intermediate nuclei, medial dorsal nuclei, cerebellum, dentatothalamocortical pathway, dentate nuclei, superior cerebellar peduncle, and corpus callosum.

19. The method of claim 11, wherein the neurologic condition is selected from the group consisting of: stroke, traumatic brain injury, neurodegenerative disease, Alzheimer's disease, Parkinson's disease, movement disorder, essential tremor, tardive dyskinesia, Tourette's syndrome, psychiatric disorder, and depression.

20. A neuromodulation apparatus comprising:
an electrode comprising an electrode contact; and
an implantable pulse generator coupled to the electrode;
wherein the pulse generator is programmed to apply an electrical signal to the electrode contact, the electrical signal comprising pulses consisting of an energy-efficient waveform selected from the group consisting of exponential increasing, exponential decreasing, and Gaussian.

21. The apparatus of claim 20, wherein the pulse generator includes a battery as a power source, and wherein the pulse generator has a battery-operated lifetime of more than 7 years when providing a continuous electrical signal to the electrode contact.

22. The apparatus of claim 20, wherein the electrode contact has a surface area of 1.25 $mm^2$ or less.

23. The apparatus of claim 20, wherein the pulse generator generates the energy-efficient waveform digitally.

24. The apparatus of claim 20, wherein the energy-efficient waveform is exponential increasing or exponential decreasing.

25. The apparatus of claim 20, wherein the energy-efficient waveform is exponential decreasing or Gaussian.

26. A non-transitory computer-readable storage medium that stores executable instructions for performing the following: obtaining a set of numeric values that define an energy-efficient waveform; and controlling a pulse generator to apply an electrical signal to an electrode contact, the electrical signal comprising pulses consisting of an energy-efficient waveform selected from the group consisting of exponential increasing, exponential decreasing and Gaussian.

* * * * *